United States Patent [19]

Vogel

[11] 3,963,761

[45] June 15, 1976

[54] PROCESS FOR THE PRODUCTION OF DINITRO-ANTHRAQUINONES

[75] Inventor: Axel Vogel, Cologne, Germany

[73] Assignee: Bayer Aktiengesellschaft, Leverkusen, Germany

[22] Filed: Sept. 4, 1974

[21] Appl. No.: 503,197

[30] Foreign Application Priority Data

Sept. 14, 1973 Germany............................ 2346317

[52] U.S. Cl. ............................................. 260/369
[51] Int. Cl.² ......................................... C07C 49/68
[58] Field of Search .................................. 260/369

[56] References Cited
UNITED STATES PATENTS

| 2,435,314 | 2/1948 | Kokatnur | 260/467 |
| 2,435,544 | 2/1948 | Kokatnur | 260/645 |
| 3,786,073 | 1/1974 | Frey et al | 260/369 |

OTHER PUBLICATIONS

Lubs, The Chemistry of Synthetic Dyes & Pigments, A.C.S. Monograph, 1955, pp. 350–351.
Houben–Weil, Methoden der Organioher Chemie; Veilag; Stuttgart, vol. 10-1, 1971, pp. 480–485.

*Primary Examiner*—Arthur P. Demers
*Attorney, Agent, or Firm*—Burgess, Dinklage & Sprung

[57] ABSTRACT

Dinitro-anthraquinones are produced by nitrating an anthraquinone in the presence of an indifferent organic solvent. As inert organic solvents there is suggested an aliphatic or alicyclic hydrocarbon having up to 12 carbon atoms and substituted once or several times by halogen or by the nitro group.

11 Claims, No Drawings

PROCESS FOR THE PRODUCTION OF DINITRO-ANTHRAQUINONES

This invention relates to a process for the production of dinitro-anthraquinones and to processes for the production and separation of 1,5- and 1,8-dinitro-anthraquinones.

It is known that dinitro-anthraquinones can be obtained by nitrating anthraquinones with nitric acid in sulphuric acid or excess nitric acid (Methoden der organischen Chemie (Houben-Weyl), 4th Edition (1971), Stuttgart, Vol. X/1, page 615; DT-OS 2,248,704). The main disadvantage of these processes, however, is that they involve the use of large quantities of materials which subsequently have to be worked up at high cost or which result in corresponding effluent pollution.

Accordingly, the object of the present invention is to provide a process for the production of dinitro-anthraquinones by nitrating anthraquinones which involves fewer pollution problems.

Although it is known that anthraquinone is preferably nitrated in the α-position, anthraquinone is relatively sluggish in reaction and is difficult to nitrate, or involves elaborate energy-consuming measures (Methoden der Organischen Chemie (Houben-Weyl), 4th Edition, (1971), Stuttgart, Vol. X/1, page 614,615). Accordingly, the nitration of anthraquinone calls for extensive ionization or a high concentration of nitronium ions such as exists, for example, in sulphuric acid (loc. cit. page 485). It is also known that only a low to very low degree of ionization into nitronium ions prevails in inert organic solvents, for example in chloroform, tetrachlormethane or nitromethane, and that nitration is actually carried out in inert organic solvents in those very cases where it is desired to carry out nitration sparingly rather than resorting to energy-consuming measures (loc. cit. page 484)

It has now surprisingly been found that dinitro-anthraquinones can be obtained in high yields by nitrating anthraquinones providing nitration is carried out in the presence of inert organic solvents. It has also been found that, on completion of nitration, 1,5- and 1,8-dinitro-anthraquinone can readily be separated, without any need to isolate the crude dinitro-anthraquinone mixture formed, by leaving from 5 to 30 mols of nitric acid, preferably from 10 to 20 mols of nitric acid, per mol of anthraquinone used in the nitration mixture on completion of nitration and, at the same time, by keeping the nitric acid: water ratio in the range of from 92 : 8 to 100 : 0, preferably from 95 : 5 to 100 : 0, separating off the undissolved, substantially pure 1,5-dinitro-anthraquinone and precipitating the 1,8-dinitro-anthraquinone from the mother liquor.

The anthraquinones do not have to be dissolved in the organic solvent for nitration. In order to obtain high volume-time yields, it is even advantageous in most cases to carry out nitration in the suspension phase. In this case the anthraquinones used are merely suspended either wholly or in part in the organic solvent used.

In the context of the invention, inert organic solvents are solvents of the kind which undergo little or no reaction with the nitrating agent under the reaction conditions.

Examples of solvents suitable for use in the process according to the invention are aliphatic and alicyclic hydrocarbons having up to 12 carbon atoms, preferably up to 6 carbon atoms, which are substituted once or several times by halogen (fluorine, chlorine, bromine or iodine) or by the nitro group. Examples of these solvents include methane, ethane, propane, butane, pentane, hexane, cyclopentane and cyclohexane. In addition to the straight-chain isomers, this list of exemplary solvents naturally includes the branched isomers and alkyl-substituted cyclo-aliphatic compounds as well.

It is preferred to use chlorine-substituted hydrocarbons, for example methylene chloride, chloroform, carbon tetrachloride, 1,1-dichlorethane, 1,2-dichlorethane, 1,1,2-trichlorethane, 1,1,2,2-tetrachlorethane, pentachlorethane, 1,2-dichlorpropane and 1,3-dichlorpropane, 1,2,3-trichlorpropane, 1,1,2,3- and 1,1,3,3-tetrachlorpropane, 1,1,1,3,3-pentachlorpropane, 1,1,1,2,3,3- and 1,1,1,2,2,3-hexachlorpropane, 1,1,1,2,2,3,3- and 1,1,1,2,3,3,3-heptachlorpropane, 1,2- and 1,4-dichlorbutane.

Examples of bromine-substituted hydrocarbons are methylene bromide, bromoform, tetrabromomethane, 1,2-dibromoethane and 1,2-dibromopropane.

Hydrocarbons of the kind substituted, for example, by fluorine or simultaneously by several halogens, for example fluortrichlormethane, difluordichlormethane, difluordibromomethane 1,1,2-trifluor-1,2,2-trichlorethane and perfluor-1,3-dimethylcyclohexane, can also be used in the process according to the invention.

Among the hydrocarbons substituted by the nitro groups, reference is made in particular to nitromethane and nitroethane.

The quantity in which the inert organic solvent is used in accordance with the invention can be varied within wide limits. It is generally used in a quantity of from 0.4 to 25 parts by volume, preferably in a quantity of from 0.6 to 10 parts by volume and, in particular, in a quantity of from 1 to 3 parts by volume, of solvent per part by weight of the anthraquinone used. Parts by volume are to parts by weight as milliliters are to grams. Nitric acid is generally used as the nitrating agent. However, it is also possible to use nitrating agents which, in addition to nitric acid, contain other strong mineral acids or Lewis acids, for example sulphuric acid, oleum, sulphur trioxide, phosphoric acid, polyphosphoric acid, phosphorus pentoxide, hydrogen fluoride or alkane sulphonic acids, for example methane sulphonic acid, trifluormethane sulphonic acid or perfluorbutane sulphonic acid. The nitric acid is generally used in a quantity of up to 50 mols, preferably in a quantity of up to 20 mols and, in particular, in a quantity of from 2 to 4 mols per mol of anthraquinone. In cases where, in addition to nitric acid, the nitrating agent contains others of the aforementioned acids, the mineral or Lewis acids are generally added in proportions of up to 5 mols, preferably in proportions of up to 4 mols and, in particular, in proportions of from 2 to 3 mols per mol of anthraquinone.

Although nitric acid having an $HNO_3$ concentration of from about 96 to 100% by weight is generally used, it is also possible to use more dilute nitric acid, i.e. nitric acid with an $HNO_3$ concentration of up to about 90% by weight, in cases where the nitrating agent simultaneously contains strong mineral or Lewis acids which are capable of binding water, for example the aforementioned acids. Mixtures of these acids can also be present in the nitrating agent.

Agents which bind the water introduced by the nitrating agent and/or the water formed during the reaction, are also preferably added to the reaction mixture. The aforementioned acids and mixtures thereof are generally used for this purpose. These agents can in turn contain as much as 4% by weight of bound water, although they preferably contain only up to 2% by weight of bound water. In general, these agents are introduced into the reaction mixture following addition of the nitrating agent, although they can also be added before or together with the nitrating agent. Some of them, for example sulphur trioxide, can also be added in the form of a solution in one of the organic solvents used in accordance with the invention. The water-binding agent is preferably used in a quantity of up to 10 mols and, in particular, in a quantity of up to 4 mols per mol of anthraquinone.

The nitration velocity decreases with increasing water content of the reaction mixture. Accordingly, it has proved to be advisable to keep the water content of the reaction mixture as low as possible, preferably below 15% by weight and, more particularly, below 10% by weight, based on the quantity of acid present.

The reaction temperature can be varied within wide limits. The reaction is preferably carried out at temperatures in the range of from −20° to +125°C, preferably at temperatures of from −15° to 105°C and, more especially, at temperatures in the range of from 0° to 80°C.

The process according to the invention is generally carried out under normal pressure, although it can also be carried out under reduced or elevated pressure. In cases where low-boiling solvents are used in the process according to the invention, it may be essential to apply elevated pressure in order to reach the temperature selected for the reaction. In general, the process according to the invention is carried out by dissolving or suspending the anthraquinones in the organic solvent, adding the nitrating agent all at once, in batches or continuously, and keeping the reaction mixture at the selected reaction temperature until the reaction is complete. The water-binding agent optionally used is also added all at once, in batches or continuously, either before, at the same time as or in admixture with the nitrating agent, or after the nitrating agent.

On the completion of the reaction, the reaction product can be isolated by various methods. For example, water can be added to the reaction mixture and the organic phase separated off, or the organic solvent can be distilled off and the substantially insoluble reaction product isolated, for example by filtration or centrifuging, from the aqueous phase. The solvent distilled off and the organic phase can be reused and recycled, respectively, the circuit optionally including a stage for working up the organic phase, for example by distillation. The measures required for this purpose are known per se. In addition, alkali liquor can be added to the aqueous solution during working up of the reaction mixture before the organic solvent is distilled off at the rate required to neutralize the acid constituents of the reaction mixture.

However, the substantially insoluble reaction product can also be directly isolated on completion of the reaction, for example by filtration or centrifuging, washed with one of the aforementioned inert organic solvents, preferably the inert organic solvent used for nitration, optionally in conjunction with highly concentrated nitric acid, and/or with water and subsequently dried. In this connection, it can be advantageous to add highly concentrated nitric acid to the organic solvent, particularly to obtain a purer reaction product. The highly concentrated nitric acid can be added to the organic solvent used for washing, although it is best added to the reaction mixture after nitration and before separation. In general, the highly concentrated nitric acid is 90 to 100% by weight HNO$_3$ and is used in a quantity of up to 75% by volume, preferably in a quantity of up to 50% by volume, and more particularly in a quantity of up to about 25% by volume of the organic solvent present.

To prepare and separate 1,5- and 1,8-dinitro-anthraquinone, the anthraquinone is first dinitrated in the manner described. The mixture of 1,5- and 1,8-dinitro-anthraquinone, which in addition contains relatively small proportions of 1,6- and 1,7-dinitro-anthraquinone, can then be isolated in the usual way. If desired, the dinitro-anthraquinone mixture washed free from acids can then be separated into a 1,5-dinitro-anthraquinone fraction and a 1,8-dinitro-anthraquinone fraction by conventional methods, for example by recrystallization from organic solvents.

However, the 1,5-/1,8-dinitro-anthraquinone mixture can also be separated without intermediate isolation of the crude product of nitration by ensuring that, on completion of nitration, the nitration mixture still contains from 5 to 30 mols, preferably from 10 to 20 mols of nitric acid per mol of anthraquinone used for nitric acid : water ratios of from 92 : 8 to 100 : 0, preferably from 95 : 5 to 100 : 0. Under these conditions, the 1,5-dinitro-anthraquinone remains substantially undissolved in the mixture of inert organic solvent and nitric acid, while at the same time the 1,8-dinitro-anthraquinone and the other secondary products of anthraquinone nitration are dissolved. The quantity of nitric acid required for separation can be added to the reaction mixture either after nitration or, preferably, at the beginning of or during nitration. The presence of nitric acid during nitration keeps the nitration products, except for the 1,5-dinitro-anthraquinone, in solution while, at the same time, the 1,5-dinitro-anthraquinone crystals grow uniformly and cleanly. The substantially pure 1,5-dinitro-anthraquinone can readily be isolated by filtration, decantation, centrifuging or similar separation techniques. It can then be washed with one of the aforementioned inert organic solvents, preferably with the inert organic solvent used for nitration, optionally in conjunction with highly concentrated nitric acid, and/or with water, and subsequently dried. In general, the highly concentrated nitric acid used is 90 to 100% by weight and preferably about 98% by weight HNO$_3$ and is employed in a quantity of up to 75% by volume, and preferably in a quantity of up to 50% by volume, of the washing solution. Separation is generally carried out at temperatures in the range of from 0° to 90°C, preferably at temperatures in the range of from 40° to 80°C.

The 1,8-dinitro-anthraquinone can be isolated from the mother liquor by various methods. For example, the solution can be cooled to temperatures of from −20° to +40°C, preferably to temperatures of from −10° to +20°C, and the precipitated 1,8-dinitro-anthraquinone can be filtered off. However, the solubility of the 1,8-dinitro-anthraquinone in the solution mixture can also be reduced by diluting the nitric acid, for example by adding water, the ratio by weight of nitric acid to water generally being adjusted to between 92 : 8 and 75 : 25 and preferably to between 90 : 10 and 85 : 15. In addition, the nitric acid can be washed out of the solution mixture, for example by adding water in a quantity of at least 35 parts by weight and preferably in a quantity of at least 50 parts by weight per 100 parts by weight of nitric acid, and hence the 1,8-dinitro-anthraquinone can be optionally precipitated together with the 1,6-/1,7 -dinitro-anthraquinone fraction. Finally, the mother liquor can also be concentrated by distillation and either the inert organic solvent and/or the nitric acid initially distilled off either wholly or in part and the 1,8-dinitro-anthraquinone can be subsequently isolated or precipitated and isolated by the methods described above.

The process according to the invention can be carried out in batches, for example in a stirrer-equipped vessel, or even continuously, for example in a cascade of vessels, in a resistance tube, in a recirculation system or in similar apparatus.

Dinitro-anthraquinones are commercial intermediate products used, for example, for the production of 1,5- and 1,8-diamino-anthraquinones, 1,5-dichloran-thraquinone, and 1,8-diphenoxy-anthraquinone, i.e. they are important intermediate products for production of a number of anthraquinone dyes.

The advantage of the process according to the invention over conventional processes is, on the one hand, the high volume-time yield obtained and, on the other hand, the fact that there is no need whatever to use mineral acids as diluents for nitrating the anthraquinones. Compared with the prior art, not only does this save mineral acid and, hence, costs, but it also solves the problems which would otherwise be involved in working up or eliminating such quantities of acid. This particular point is of special significance in view of the increasing requirements regarding pollution control and, in itself, substantiates the advance of the process according to the invention over the prior art.

In addition, the inert organic solvent used in the process according to the invention can be re-used either directly or, optionally, after working up, for example by distillation. The water-containing acid phase which is substantially free from dissolved secondary products can also be regenerated by adding the aforementioned water-binding agents or, for example, corresponding acid anhydrides and recycled. This affords the additional advantage over the already proposed reuse of the mineral acids employed as solvent that the quantities of highly concentrated mineral acids which have to be handled are much smaller, there is no need for complicated working-up to remove dissolved secondary products, nor are there any corrosion problems.

The reaction product obtained also contains smaller quantities of secondary products than is the case in the prior art, and accumulates in a form which enables further purification known per se to be carried out particularly easily and effectively.

In the following Examples, percentages are by weight unless otherwise stated. Where quantities are quoted in percent for mineral acids, the balance is water.

EXAMPLE 1

180 ml of 98 % by weight nitric acid are added at 0°C to a suspension of 250 g of anthraquinone in 400 ml of methylene chloride. 141 ml of 20 % oleum are then added dropwise over a period of 2 hours at 0°C and the reaction mixture is subsequently stirred first for 3 hours at that temperature and then for 10 hours at around 54°C. The reaction mixture is then poured into 1000 ml of water, the methylene chloride is distilled off and the dinitro-anthraquinone mixture is isolated by filtration. After washing and drying, the yield is 357 g. The product contains 40% of 1,5-dinitro-anthraquinone and 37 % of 1,8-dinitro-anthraquinone (altogether 77% of the theoretical amount of $\alpha,\alpha'$-dinitro-anthraquinone). The product also contains 9% of 1,6-dinitro-anthraquinone and 9% of 1,7-dinitro-anthraquinone.

EXAMPLE 2

180 ml of 98% by weight nitric acid are added at 0°C to a suspension of 250 g of anthraquinone in 400 ml of methylene chloride. 200 ml of 100% by weight sulphuric acid are then added dropwise over a period of 2 hours at 0°C, and the reaction mixture is subsequently stirred first for 3 hours at that temperature and then for 10 hours at around 54°C. The reaction mixture is then poured into 1000 ml of water, the methylene chloride is distilled off and the dinitro-anthraquinone mixture is isolated by filtration. After washing and drying, the yield is 353 g. The product contains 40% of 1,5-dinitro-anthraquinone and 37% of 1,8-dinitro-anthraquinone.

EXAMPLE 3

200 ml of 98% by weight nitric acid are added at 0°C to a suspension of 250 g of anthraquinone in 400 ml of 1,2-dichlorethane. 141 ml of 20% oleum are then added dropwise over a period of 2 hours at 0°C, and the reaction mixture is stirred first for 4 hours at 0°C and then for 1 hour at 80°C. The reaction mixture is subsequently diluted with 1000 ml of water, the 1,2-dichlorethane is distilled off and the dinitro-anthraquinone mixture is isolated by filtration. After washing and drying, the yield is 355 g. The product contains 41% of 1,5-dinitro-anthraquinone and 38% of 1,8-dinitro-anthraquinone.

EXAMPLE 4

100 ml of 98% nitric acid are added at 42°C to a suspension of 62.4 g of anthraquinone in 100 ml of methylene chloride. 40 ml of 100% sulphuric acid are then added dropwise over a period of 30 minutes and the mixture is stirred for another 5 hours at 42°C. The insoluble fraction is filtered off under suction at 40°C, washed with 200 ml of methylene chloride and then with water and dried. The yield is 57.0 g of dinitro-anthraquinone mixture, which comprises 57% of 1,5-dinitro-anthraquinone and 40% of 1,8-dinitro-anthraquinone.

EXAMPLE 5

250 g of anthraquinone are suspended in 200 ml of methylene chloride, followed by the addition at 45°C of 180 ml of 98% nitric acid. 182 ml of 20% oleum are then added dropwise over a period of 3 hours at 45°C, followed by stirring at that temperature for another 4 hours. The mixture is then allowed to cool to 20°C, after which the insoluble fraction is filtered off. The filter residue is washed first with 200 ml of methylene chloride and then with water until neutral, and dried. The yield is 327 g of dinitro-anthraquinone containing 43% of 1,5-dinitro-anthraquinone and 38% of 1,8-dinitro-anthraquinone, in addition to 7% of 1,6-dinitro-anthraquinone and 10% of 1,7-dinitro-anthraquinone.

EXAMPLE 6

200 ml of 98% nitric acid are added over a period of 1 hour at reflux temperature to 62.4 g of anthraquinone in 100 ml of methylene chloride. 40 ml of 20% oleum are added dropwise over a period of 1 hour, and the reaction mixture is stirred for another 3 hours at reflux temperature. The mixture is then poured into 500 ml of water, the methylene chloride is distilled off and the precipitate is filtered off. The yield of dinitro-anthraquinone is then 87.3 g. 41% of the product consists of 1,5-dinitro-anthraquinone, 38% of 1,8-dinitro-anthraquinone, 8.8% of 1,6-dinitro-anthraquinone and 9.4% of 1,7-dinitro-anthraquinone.

EXAMPLE 7

62.4 g of anthraquinone are introduced over a period of 15 minutes at −15°C into a mixture of 100 ml of methylene chloride and 200 ml of 98% by weight nitric acid. The reaction mixture is then stirred for 2 hours at −15°C, 40 ml of 100% by weight sulphuric acid are added dropwise over a period of 1 hour at −15°C and the mixture is subsequently heated for 3 hours to 50°C. For working up, the reaction mixture is poured into 500 ml of water, the methylene chloride is distilled off and the dinitro-anthraquinones are isolated by filtration, washing and drying. The yield is 88.2 g of dry product containing 44% of 1,5-dinitro-anthraquinone, 41% of 1,8-dinitro-anthraquinone, 6.2% of 1,6-dinitro-anthraquinone and 6.5 % of 1,7-dinitro-anthraquinone.

EXAMPLE 8

62.4g of anthraquinone are suspended in 100 ml of methylene chloride, followed by the addition of 200 ml of 98% by weight nitric acid over a period of 30 minutes at −15°C. 35 ml of 20% oleum are then added dropwise over a period of 1 hour at −15°C, and the reaction mixture is stirred for 3 hours at that temperature. After stirring for another 2 hours at reflux temperature (52°C), the insoluble fraction is filtered at 40°C and washed with 2 × 100 ml portions of methylene chloride and then with water. After drying, the yield is 33.8 g. 96.0% by weight of the product consists of 1,5-dinitro-anthraquinone and 4.0% by weight of 1,8-dinitro-anthraquinone. Other isomers or 1-nitroanthraquinone or 2-nitroanthraquinone are present in a quantity of less than 0.25%.

The mother liquor is subjected to fractional distillation, the methylene chloride initially being distilled off at normal pressure, and a 98% by weight nitric acid subsequently being distilled off under reduced pressure. Following the removal of 53 ml of 98% by weight nitric acid, distillation is stopped and the sump is filtered off at 50°C through a glass frit. The precipitate is then washed and dried, giving a yield of 36.7 g. 84.0% by weight of the product consists of 1,8-dinitro-anthraquinone, 13.6% by weight of 1,5-dinitro-anthraquinone, 0.4% by weight of 1,6-dinitro-anthraquinone and 0.8% by weight of 1,7-dinitro-anthraquinone.

EXAMPLE 9

544 g of a nitration acid containing 38.0% by weight of nitric acid and 61.5% by weight of sulphuric acid are added over a period of about 90 minutes at reflux temperature to a suspension of 250 g of anthraquinone in 400 ml of methylene chloride. The mixture is then stirred for 6 hours at reflux temperature, subsequently poured into 1000 ml of water and the methylene chloride is distilled off. Filtration under suction, washing and drying leaves 355 g of a dinitro-anthraquinone mixture containing 35% of 1,5-dinitro-anthraquinone and 31% of 1,8-dinitro-anthraquinone.

EXAMPLE 10

575 g of a nitration acid containing 41.2% by weight of nitric acid and 58.0% by weight of sulphuric acid are added over a period of about 90 minutes at 40°C to a suspension of 250 g of anthraquinone in 400 ml of 1,2-dichlorethane. The mixture is stirred for 6 hours at 40°C, subsequently poured into 1000 ml of water and the 1,2-dichlorethane is distilled off. Filtration under suction, washing and drying leaves 356 g of a dinitro-anthraquinone mixture containing 38% of 1,5-dinitro-anthraquinone and 34% of 1,8-dinitro-anthraquinone.

EXAMPLE 11

62.4 g of anthraquinone are suspended in 100 ml of methylene chloride at −15°C and 200 ml of 98% by weight nitric acid are added, followed by the dropwise addition over a period of 1 hour at −15°C of 35 ml of 20% oleum. The mixture is then stirred first for 3 hours at −15°C and then for 2 hours at 52°C, and the insoluble fraction is filtered off at 40°C. Washing with methylene chloride and water, followed by drying, leaves 33.6 g of 96% by weight 1,5-dinitro-anthraquinone. The mother liquor is poured into 500 ml of water and the methylene chloride is distilled off. The precipitated deposit is filtered off under suction, washed with water until neutral and dried, giving 54.5 g of 66% by weight 1,8-dinitro-anthraquinone.

EXAMPLE 12

62.4 g of anthraquinone are dinitrated in the same way as described in Example 8. The 1,5-dinitro-anthraquinone is separated off and the 1,8-dinitro-anthraquinone is precipitated from the mother liquor by stirring in 20 ml of water. After filtration at 20°C the product is washed with 50 ml of methylene chloride and then with water and is subsequently dried. 14.8 g of 93.8% 1,8-dinitro-anthraquinone are obtained. The other analytical data are summarized in Table 1.

EXAMPLE 13

62.4 g of anthraquinone are dinitrated in the same way as described in Example 8. Following separation of the 1,5-dinitro-anthraquinone fraction, the 1,8-dinitro-anthraquinone fraction is precipitated from the mother liquor by stirring in 35 ml of water. After filtration at 20°C, the product is washed first with 50 ml of methylene chloride and then with water and is subsequently dried, giving 33.1 g of an 86.1% 1,8-dinitro-anthraquinone (fraction A). A 1,6-/1,7-dinitro-anthraquinone fraction (fraction B) can be recovered from the filtrate in a quantity of 21.3 g by adding 500 ml of water, distilling the methylene chloride and filtering the deposit. The analytical data are summarized in Table 1.

EXAMPLE 14

62.4 g of anthraquinone are dinitrated in the same way as described in Example 8. Following separation of the 1,5-dinitro-anthraquinone fraction, the methylene chloride is distilled off from the mother liquor under normal pressure, and 29 ml of 98% by weight nitric acid are distilled off in vacuo. The distillation sump is poured at 50°C onto a filter, filtered under suction and the filter cake is washed with water until neutral and then dried. 26.8 g of a 92.1% 1,8-dinitro-anthraquinone (fraction A) are isolated. Another dinitroanthraquinone fraction (B) can be recovered from the filtrate in a quantity of 27.2 g by the addition of 500 ml of water. The analytical data are summarized in Table 1.

EXAMPLE 15

62.4 g of anthraquinone are suspended in 100 ml of methylene chloride, followed by the addition of 250 ml of 98% by weight nitric acid over a period of 30 minutes at −15°C. 35 ml of 20% oleum are then added dropwise over a period of 1 hour at −15°C, followed by stirring first for 3 hours at −15°C and then for 2 hours at reflux temperature. The mixture is then cooled to 40°C and the deposit is filtered off and washed with 2 × 100 ml portions of methylene chloride and then with water. After drying, the yield is 30.0 g of a product containing 96.7% of 1,5-dinitro-anthraquinone and 3.2% of 1,8-dinitro-anthraquinone.

EXAMPLE 16

250 ml of 98% by weight nitric acid are added at 40°C to a suspension of 250 g of anthraquinone in 400 ml of 1,2-dichlorpropane. 141 ml of 20% oleum are then added dropwise over a period of 2 hours, and the mixture is stirred first for 4 hours at 40°C and then for 2 hours at 80°C. The mixture is then diluted with 1000 ml of water, the 1,2-dichlorpropane is distilled off and the dinitro-anthraquinone mixture is isolated by filtration. After washing and drying, the yield comprises 340 g of a product containing 37% of 1,5-dinitro-anthraquinone, 33% of 1,8-dinitro-anthraquinone, 10% of 1,6-dinitro-anthraquinone and 10% of 1,7- dinitroanthraquinone.

EXAMPLE 17

250 ml of 98% by weight nitric acid are added at 40°C to a suspension of 250 g of anthraquinone in 1000 ml of 1,1,2,2-tetrachlorethane. 141 ml of 20% oleum are then added dropwise over a period of 2 hours, followed by stirring first for 4 hours at 40°C and then for 2 hours at 80°C. The mixture is diluted with 2000 ml of water, the tetrachlorethane is distilled off and the dinitro-anthraquinone mixture is isolated by filtration. The yield of dry product is 355 g, the product containing 40% of 1,5-dinitro-anthraquinone, 36% of 1,8-dinitro-anthraquinone and 10% each of 1,6- and 1,7-dinitro-anthraquinone.

EXAMPLE 18

62.4 g of anthraquinone are dispersed in 250 ml of nitromethane followed by the addition of 65 ml of 98% by weight nitric acid. 80 ml of 100% by weight sulphuric acid are added dropwise over a period of 1 hour at 40°C, followed by stirring for another 6 hours at that temperature. The deposit is filtered off at room temperature, washed with 100 ml of nitromethane and then with water and subsequently dried. The yield is 79.7 g. 43% of the product consists of 1,5-dinitro-anthraquinone and 38% of 1,8-dinitro-anthraquinone.

Table 1

| Example No. | Fraction | dinitro-anthraquinone content | | | |
|---|---|---|---|---|---|
| | | 1,5− | 1,8− | 1,6− | 1,7− |
| 12 | — | 5.8% | 93.8% | 0.4% | 0.3% |
| 13 | A | 12.2% | 86.1% | 0.5% | 0.3% |
| | B | 6.6% | 44.3% | 22.6% | 23.5% |
| 14 | A | 6.8% | 92.1% | 0.4% | 0.5% |
| | B | 12.7% | 44.1% | 18.0% | 19.2% |

What is claimed is:

1. Process for the production of dinitro-anthraquinones, which comprises nitrating an anthraquinone in the presence of from 0.4 to 25 by volume, per part by weight of the anthraquinone, of an inert inorganic solvent which is an aliphatic or alicyclic hydrocarbon having up to 12 carbon atoms and substituted once or several times by halogen or by the nitro group.

2. Process of claim 1, wherein the inert organic solvent is an aliphatic or alicyclic hydrocarbon having up to 6 carbon atoms and substituted once or several times by halogen or by the nitro group.

3. Process of claim 1, wherein the inert organic solvent is an aliphatic chlorinated hydrocarbon having up to 6 carbon atoms.

4. Process of claim 1, wherein the inert organic solvent is methylene chloride, 1,2-dichlorethane, 1,1,2,2-tetrachlorethane or 1,2-dichlorpropane.

5. Process of claim 1, wherein the inert organic solvent is nitro-methane or nitroethane.

6. Process of claim 1, wherein the inert organic solvent is used in a quantity of from 0.6 to 10 parts by volume per part by weight of the anthraquinone.

7. Process of claim 1, wherein nitration is effected with from 2 to 20 mols of nitric acid and from 2 to 4 mols of sulphuric acid or oleum per mol of anthraquinone.

8. Process for the production and separation of 1,5- and 1,8-dinitro-anthraquinone, in accordance with claim 1, wherein the nitration agent contains sufficient nitric acid so that, on completion of nitration, the nitration mixture contains from 10 to 20 mols of nitric acid per mol of anthraquinone used; and including the further steps of separating off the substantially insoluble 1,5-dinitroanthraquinone; and isolating the 1,8-dinitroanthraquinone from the mother liquor.

9. Process of claim 8, wherein the 1,8-dinitroanthraquinone is precipitated from the mother liquor by the addition of water.

10. Process of claim 8, wherein the 1,8-dinitroanthraquinone is precipitated from the mother liquor by partly distilling the nitric acid from the mother liquor.

11. Process of claim 8, wherein the nitration agent also contains 2 to 4 mols of sulphuric acid or oleum per mol of anthraquinone, and the inert solvent is methylene chloride, 1,2-dichloroethane, 1,1,2,2-tetrachlorethane, 1,2-dichlorpropane, nitromethane or nitroethane and is used in about 0.6 to 10 parts by volume per part by weight of the anthraquinone.

* * * * *